United States Patent
Iloeje et al.

(10) Patent No.: US 11,806,322 B2
(45) Date of Patent: Nov. 7, 2023

(54) MIRDAMETINIB TREATMENT

(71) Applicant: SpringWorks Therapeutics Inc., Stamford, CT (US)

(72) Inventors: Uchenna H Iloeje, Stamford, CT (US); Abraham J Langseth, Stamford, CT (US); Todd Shearer, Stamford, CT (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 0 days.

(21) Appl. No.: 18/185,148

(22) Filed: Mar. 16, 2023

(65) Prior Publication Data
US 2023/0321013 A1 Oct. 12, 2023

Related U.S. Application Data

(60) Provisional application No. 63/321,036, filed on Mar. 17, 2022, provisional application No. 63/321,046, filed on Mar. 17, 2022.

(51) Int. Cl.
*A61K 31/166* (2006.01)
*A61P 35/00* (2006.01)
*A61K 9/00* (2006.01)

(52) U.S. Cl.
CPC .......... *A61K 31/166* (2013.01); *A61K 9/0053* (2013.01); *A61P 35/00* (2018.01)

(58) Field of Classification Search
CPC ...... A61P 35/00; A61K 31/166; A61K 9/0053
See application file for complete search history.

(56) References Cited

U.S. PATENT DOCUMENTS

| | | |
|---|---|---|
| 11,427,534 B1 | 8/2022 | Patterson et al. |
| 11,453,641 B2 | 9/2022 | Irdam |

OTHER PUBLICATIONS

Weiss, et al., NF106: A Neurofibromatosis Clinical Trials Consortium Phase II Trial of the MEK Inhibitor Mirdametinib (PD-0325901) in Adolescents and Adults With NF1-Related Plexiform Neurofibromas, J. of Clin. Oncol., vol. 39, Issue 7, pp. 797-806 (2021) (Year: 2021).*
Weiss et al., J. Clin. Oncol., 29, 797-806, 2021.

* cited by examiner

*Primary Examiner* — Erich A Leeser
(74) *Attorney, Agent, or Firm* — Blank Rome LLP

(57) ABSTRACT

The present disclosure relates to a method for treating certain types of tumors or cancers, such as plexiform neurofibromas (PN), plexiform neurofibromas associated with neurofibromatosis type 1 (NF1-PN), by orally administering an effective amount of mirdametinib to the patient, where an amount of mirdametinib is administered on the first day of treatment to provide (i) an $AUC_{0-tau}$ less than 400 ng·h/mL, (ii) a $C_{max}$ no more than 40 ng/mL, or (iii) both.

26 Claims, No Drawings

MIRDAMETINIB TREATMENT

The present application claims the benefit of U.S. Provisional Application Nos. 63/321,036, filed Mar. 17, 2022, and 63/321,046, filed Mar. 17, 2022, each of which is hereby incorporated by reference in its entirety.

FIELD OF THE INVENTION

The present disclosure relates to a method for treating certain types of tumors or cancers, such as plexiform neurofibromas (PN), plexiform neurofibromas associated with neurofibromatosis type 1 (NF1-PN), by orally administering an effective amount of mirdametinib to the patient, where an amount of mirdametinib is administered on the first day of treatment to provide (i) an $AUC_{0-tau}$ less than 400 ng·h/mL, (ii) a $C_{max}$ no more than 40 ng/mL, or (iii) both.

BACKGROUND

Mirdametinib is an allosteric, small molecule targeting mitogen-activated protein kinase kinase (MEK).

Weiss describes a Phase II clinical trial of mirdametinib in subjects with neurofibromatosis type 1 who have a plexiform neurofibroma (Weiss et al., J. Clin. Oncol., 29, 797-806, 2021).

There is a continuing need for improved treatments for tumors and cancers, including NF1-PN.

BRIEF SUMMARY OF THE INVENTION

One aspect of the present invention relates to a method of treating a patient (e.g., a human patient) 2 years or older who has neurofibromatosis type 1 (NF1) associated inoperable plexiform neurofibromas (PN) by orally administering an effective amount of mirdametinib to the patient, where an amount of mirdametinib is administered on the first day of treatment to provide an $AUC_{0-tau}$ less than 400 ng·h/mL. It has been discovered that lower amounts of mirdametinib may be administered to effectively treat patients having a tumor or cancer, such as NF1-PN, with reduced toxicity. In one embodiment, the patient continues to be administered the mirdametinib to provide an $AUC_{0-tau}$ less than 400 ng·h/mL. In one embodiment, the patient has symptomatic, inoperable plexiform neurofibromas.

Another embodiment is a method of treating a patient 2 years or older who has NF1 associated inoperable PN that is progressing or causing significant morbidity by orally administering an effective amount of mirdametinib to the patient, where an amount of mirdametinib is administered on the first day of treatment to provide an $AUC_{0-tau}$ less than 400 ng·h/mL. In one embodiment, the patient continues to be administered the mirdametinib to provide an $AUC_{0-tau}$ less than 400 ng·h/mL.

Yet another embodiment is a method of treating a human patient 2 years or older who has neurofibromatosis type 1 (NF1) associated inoperable plexiform neurofibromas (PN) by orally administering on the first day of treatment 1 mg of mirdametinib twice daily to the patient to achieve an $AUC_{0-tau}$ less than 400 ng·h/mL.

Yet another embodiment is a method of treating a human patient 2 years or older who has neurofibromatosis type 1 (NF1) associated inoperable plexiform neurofibromas (PN) comprising orally administering on the first day of treatment 1 mg of mirdametinib twice daily to the patient to provide a $C_{max}$ no more than 40 ng/mL.

Yet another embodiment is a method of treating a human patient 8 years or older who has neurofibromatosis type 1 (NF1) associated inoperable plexiform neurofibromas (PN) comprising orally administering an effective amount of mirdametinib to the patient, wherein an amount of mirdametinib is administered on the first day of treatment to provide (i) an $AUC_{0-tau}$ less than 400 ng·h/mL, (ii) a $C_{max}$ no more than 40 ng/mL, or (iii) both, wherein, during treatment, the patient suffers from acneiform rash and is topically treated (or administered) with clindamycin. In one embodiment, the patient suffers from pustular rash. In one embodiment, the patient continues to be administered the mirdametinib to provide an $AUC_{0-tau}$ less than 400 ng·h/mL.

Yet another embodiment is a method of treating a tumor or cancer in a patient (e.g., a human patient) by orally administering an effective amount of mirdametinib to the patient, wherein an amount of mirdametinib is administered on the first day of treatment to provide (i) an $AUC_{0-tau}$ less than 400 ng·h/mL, (ii) a $C_{max}$ no more than 40 ng/mL, or (iii) both. In one embodiment, the patient continues to be administered the mirdametinib to provide (i) an $AUC_{0-tau}$ less than 400 ng·h/mL, (ii) a $C_{max}$ no more than 40 ng/mL, or (iii) both. In one embodiment, the tumor or cancer is selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain. In one embodiment, the tumor or cancer is plexiform neurofibromas. In another embodiment, the tumor or cancer is plexiform neurofibromas associated with neurofibromatosis type 1. In yet another embodiment, the tumor or cancer is high grade glioma. In yet another embodiment, the high grade glioma is a primary cancer. In yet another embodiment, the high grade glioma is a metastatic cancer. In yet another embodiment, the tumor or cancer is low grade ovarian cancer. In yet another embodiment, the tumor or cancer is Langerhans cell histiocytosis. In yet another embodiment, the tumor or cancer is brain cancer. In yet another embodiment, the tumor or cancer is a cancer that has metastasized to the patient's brain including lung cancer, breast cancer and melanoma.

Yet another embodiment is a method of treating a human patient 2 years or older who has neurofibromatosis type 1 (NF1) associated inoperable plexiform neurofibromas (PN) by orally administering an effective amount of mirdametinib to the patient, where an amount of mirdametinib is administered on the first day of treatment to provide a $C_{max}$ no more than 40 ng/mL.

Yet another embodiment is a method of treating a human patient 2 years or older who has neurofibromatosis type 1 (NF1) associated inoperable plexiform neurofibromas (PN) that is progressing or causing significant morbidity by orally administering an effective amount of mirdametinib to the patient, where an amount of mirdametinib is administered on the first day of treatment to provide a $C_{max}$ no more than 40 ng/mL. In one embodiment, an amount of mirdametinib is administered on the first day of treatment to provide a $C_{max}$ no more than 32 ng/mL. In another embodiment, an amount of mirdametinib is administered on the first day of treatment to provide a $C_{max}$ no more than 30 ng/mL.

Yet another embodiment is a method of treating a human patient at least 2 years of age who has neurofibromatosis type 1 (NF1) associated inoperable plexiform neurofibromas (PN) comprising
  (a) selecting mirdametinib as a treatment for the patient at least partially based on its objective response rate, where the objective response rate is defined as at least a 20% decrease in tumor size using centrally read MRI volumetric analysis, and (b) upon selection of mirdametinib as a treatment, orally administering an effective amount of mirdametinib to the patient. In one embodiment, in step (a), mirdametinib is selected based on a response rate of at least 70%. In another embodiment, in step (i), mirdametinib is selected based on a response rate of at least 75%. In yet another embodiment, in step (i), mirdametinib is selected based on a response rate of at least 80%. In yet another embodiment, in step (i), mirdametinib is selected based on a response rate of at least 85%. In yet another embodiment, in step (i), mirdametinib is selected based on a response rate of at least 90%. In yet another embodiment, in step (i), mirdametinib is selected based on a response rate of at least 95%.

In one embodiment of any of the methods described herein, an amount of mirdametinib is administered on the first day of treatment to provide an $AUC_{0-tau}$ less than 200 ng·h/mL. In one embodiment, the patient continues to be administered the mirdametinib to provide an $AUC_{0-tau}$ less than 200 ng·h/mL.

In one embodiment of any of the methods described herein, an amount of mirdametinib is administered on the first day of treatment to provide an $AUC_{0-tau}$ less than 100 ng·h/mL. In one embodiment, the patient continues to be administered the mirdametinib to provide an $AUC_{0-tau}$ less than 100 ng·h/mL.

In one embodiment of any of the methods described herein, the patient has symptomatic, inoperable plexiform neurofibromas (PNs).

In one embodiment of any of the methods described herein, the patient has progressive PN.

In one embodiment of any of the methods described herein, the patient has PNs that cause significant morbidity.

In one embodiment of any of the methods described herein, the patient (e.g., NF1-PN patient) has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function, or painful lesions. In one embodiment, the lesions causing major deformity or are significantly disfiguring are tumors of the head and neck or those on other areas of the body that are unable to be concealed by standard garments. In one embodiment of any of the methods described herein, the patient has paraspinal lesions.

In one embodiment of any of the methods described herein, the patient has the clinical diagnosis of NF1 using the NIH Consensus Conference and one or more of the following:

(a) six or more café-au-lait macules with a diameter >5 mm in prepubertal and >15 mm in post-pubertal individuals;
(b) freckling in axilla or inguinal regions;
(c) optic glioma;
(d) two or more Lisch nodules;
(e) a distinctive bony lesion (dysplasia of the sphenoid bone or dysplasia of thinning of long bone cortex); and
(f) a first degree relative with NF1.

In one embodiment of any of the methods described herein, the patient has a constitutional NF1 mutation documented in a Clinical Laboratory Improvement Amendments/College of American Pathologists certified lab.

In one embodiment of any of the methods described herein, the patient either (a) has a parent diagnosed with NF1 and one or more criteria of (1) through (7) or (b) does not have a parent diagnosed with NF1 but has two or more criteria of (1) through (7):

(1) six or more café-au-lait macules over 5 mm in greatest diameter in prepubertal individuals and over 15 mm in greatest diameter in post-pubertal individuals;
(2) freckling in the axillary or inguinal region;
(3) two or more neurofibromas of any type or one plexiform neurofibroma
(4) optic pathway glioma;
(5) two or more iris Lisch nodules identified by slit lamp examination or two or more choroidal abnormalities (defined as bright, patchy nodules imaged by optical coherence tomography (OCT)/near-infrared reflectance (NIR) imaging;
(6) a distinctive osseus lesion (such as sphenoid dysplasia, anterolateral bowing of the tibia, or pseudarthrosis of a long bone); and
(7) a heterozygous pathogenic NF1 variant with a variant allele fraction of 50% in apparently normal tissue such as white blood cells.

In one embodiment of any of the methods described herein, (a) for a patient having a body surface area no more than 0.69 $m^2$, the patient is initially administered 1 mg mirdametinib twice daily,
(b) for a patient having a body surface area of 0.7 to 1.04 $m^2$, the patient is initially administered 2 mg mirdametinib twice daily,
(c) for a patient having a body surface area of 1.05 to 1.49 $m^2$, the patient is initially administered 3 mg mirdametinib twice daily, and
(d) for a patient having a body surface area of at least 1.5 $m^2$, the patient is initially administered 4 mg mirdametinib twice daily.

In one embodiment of any of the methods described herein, the initial dosage regimen is continued to be used, unless for instance, a severe adverse event occurs requiring reduction in the dosage regimen.

In one embodiment of any of the methods described herein, the maximum daily dose is 4 mg mirdametinib twice daily.

In one embodiment of any of the methods described herein, over each four week period, the mirdametinib is administered for the first three weeks and discontinued for the last one week.

In one embodiment of any of the methods described herein, the patient has at least a 20% reduction in plexiform neurofibroma volume as determined by volumetric magnetic resonance imaging analysis following treatment with mirdametinib.

In one embodiment of any of the methods described herein, the treatment results in decreased pain intensity.

In one embodiment of any of the methods described herein, the treatment results in decreased pain interference.

In one embodiment of any of the methods described herein, the dose administered is reduced due to an adverse event, wherein the dose is reduced as follows:

(a) if the dose at the time of the event is 1 mg mirdametinib twice daily, then the reduced daily dose is 1 mg administered in the morning only;
(b) if the dose at the time of the event is 2 mg mirdametinib twice daily, then the reduced daily dose is 2 mg administered in the morning and 1 mg administered in the afternoon or evening;

(c) if the dose at the time of the event is 3 mg mirdametinib twice daily, then the reduced daily dose is 2 mg administered twice daily; and (d) if the dose at the time of the event is 4 mg mirdametinib twice daily, then the reduced daily dose is 3 mg administered twice daily. In one embodiment, the adverse event resulting in the dose reduction is acneiform.

In one embodiment of any of the methods described herein, during treatment, the patient is topically administered clindamycin to treat the acneiform.

In one embodiment of any of the methods described herein, the patient is at least 2 years of age. In one embodiment, the patient has an age of ≥2 and <25. In yet another embodiment of any of the methods described herein, the patient is 2 to 15 years of age.

In one embodiment of any of the methods described herein, the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis. In one embodiment, in step (i), mirdametinib is selected based on a response rate of at least 70%. In another embodiment, in step (i), mirdametinib is selected based on a response rate of at least 75%. In yet another embodiment, in step (i), mirdametinib is selected based on a response rate of at least 80%. In yet another embodiment, in step (i), mirdametinib is selected based on a response rate of at least 85%. In yet another embodiment, in step (i), mirdametinib is selected based on a response rate of at least 90%. In yet another embodiment, in step (i), mirdametinib is selected based on a response rate of at least 95%.

In some aspects, a therapeutically effective amount of mirdametinib, or a pharmaceutically acceptable salt thereof, is administered. In some aspects, the mirdametinib, or a pharmaceutically acceptable salt thereof, is administered in an amount of about 1 mg/m$^2$ to about 10 mg/m$^2$ per day based on mirdametinib free base. In some aspects, the mirdametinib, or a pharmaceutically acceptable salt thereof, is administered in an amount of about 1 mg to about 10 mg per day based on mirdametinib free base.

In some aspects, the mirdametinib, or a pharmaceutically acceptable salt thereof, is administered in a single dosage form comprising about 0.1 mg/m$^2$ to about 10 mg/m$^2$ based on mirdametinib free base. In some aspects, the mirdametinib, or a pharmaceutically acceptable salt thereof, is administered in a single dosage form comprising about 0.1 mg to about 10 mg based on mirdametinib free base.

In some aspects, the mirdametinib, or a pharmaceutically acceptable salt thereof, is administered once daily. In some aspects, the mirdametinib, or a pharmaceutically acceptable salt thereof, is administered twice daily.

In some aspects, the mirdametinib, or a pharmaceutically acceptable salt thereof, exhibits high blood-brain-barrier penetration.

In one embodiment of any of the methods described herein, the human patient has had no prior exposure to MEK inhibitors.

In one embodiment of any of the methods described herein, the mirdametinib, or a pharmaceutically acceptable salt thereof, is administered orally. In some aspects, the mirdametinib, or a pharmaceutically acceptable salt thereof, is dispersible in a potable liquid or orodispersible in a patient's saliva. In some aspects, the mirdametinib, or a pharmaceutically acceptable salt thereof, is administered orally as a solid dosage form. In some aspects, the solid dosage form is a tablet or capsule. In some aspects, the solid dosage form is a capsule.

In one embodiment of any of the methods described herein, the mirdametinib, or a pharmaceutically acceptable salt thereof, is administered as a monotherapy to treat the tumor or cancer. In some aspects, the mirdametinib, or a pharmaceutically acceptable salt thereof, is administered in combination with another active ingredient and/or surgery to treat the tumor or cancer.

In one embodiment of any of the methods described herein, the mirdametinib is mirdametinib free base.

Yet another embodiment is an oral pharmaceutical composition comprising 1 mg mirdametinib, where the composition provides, upon initial oral administration to a human subject who has just initiated treatment with mirdametinib, an $AUC_{0\text{-}tau}$ less than 400 ng·h/mL. In one embodiment, the composition provides, upon initial oral administration to a human subject who has just initiated treatment with mirdametinib, an $AUC_{0\text{-}tau}$ less than 375, 350, 325, 300, 275, 250, 225, 200, 175, 150, 125, or 100 ng·h/mL.

Yet another embodiment is an oral pharmaceutical composition comprising 1 mg mirdametinib, where the composition provides, upon initial oral administration to a human subject who has just initiated treatment with mirdametinib, a $C_{max}$ no more than 40 ng/mL. In one embodiment, the composition provides, upon initial oral administration to a human subject who has just initiated treatment with mirdametinib, a $C_{max}$ no more than 38, 36, 34, 32, 30, or 28 ng/mL.

In one embodiment of any of the compositions described herein, the mirdametinib is mirdametinib free base.

DETAILED DESCRIPTION OF THE INVENTION

Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "mirdametinib" refers to the single enantiomer N-((R)-2,3-dihydroxypropoxy)-3,4-difluoro-2-(2-fluoro-4- iodo-phenylamino)-benzamide. The teachings throughout the specification regarding mirdametinib equally apply to pharmaceutically acceptable salts of mirdametinib. For instance, the disclosure of a method of treating neurofibromatosis type 1 (NF1) associated inoperable plexiform neurofibromas (PN) with mirdametinib also means that a pharmaceutically acceptable salt of mirdametinib can be administered to treat NF1 associated inoperable PN.

The term "mg/m$^2$" refers to the dose in milligrams per m$^2$ body surface area of the patient.

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject. The patient may be a pediatric patient.

The term "pediatric" refers to a human subject under the age of 21 years at the time of treatment. The term "pediatric" can be further divided into various subpopulations including: neonates (from birth through the first 28 days of life); infants (29 days of age to less than two years of age); children (two years of age to less than 12 years of age); and adolescents (12 years of age through 21 years of age (up to, but not including, the twenty-second birthday)). See, e.g., Berhman R E, Kliegman R, Arvin A M, Nelson W E. Nelson Textbook of Pediatrics, 15th Ed. Philadelphia: W. B. Saunders Company, 1996; Rudolph A M, et al. Rudolph's Pediatrics, 21st Ed. New York: McGraw-Hill, 2002; and Avery M D, First L R. Pediatric Medicine, 2nd Ed. Baltimore: Williams & Wilkins; 1994. Younger pediatric patients in particular, such as neonates, infants and young children, can have difficulty swallowing whole capsules or tablets.

The term "$AUC_{0-tau}$" refers to the area under the plasma concentration-time curve from time 0 to the end of the dosing interval. For a twice daily drug, the dosing interval would be 0-12 hours.

The term "$C_{max}$" refers to the maximum plasma concentration.

The term "dispersible" as used herein refers to a composition (e.g., a tablet, powder, granules, minitablets, or pellets) which disintegrates and/or dissolves when combined with water or another potable liquid (e.g., a non-water beverage), or a subject's own saliva when placed in the subject's mouth, with or without the addition of agitation or temperature modification. In some aspects, the dispersible composition disintegrates or dissolves within 10 minutes, 9 minutes, 8 minutes, 7 minutes, 6 minutes, 5 minutes, 4 minutes, 3 minutes, 2 minutes, or 1 minute after being combined with water or another potable liquid. Such disintegration or dissolution need not be complete. For example, a dispersible tablet may dissolve almost entirely, but some undissolved particulate matter may remain.

The term "orodispersible" refers to a composition which is capable of dissolving or disintegrating in a subject's mouth (i.e., dissolving or disintegrating in a subject's saliva) if administered orally, without a requirement of first dissolving or disintegrating in a separate container.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for a tumor, according to the methods described herein if the patient shows one or more of the following: a reduction in the size of the tumor; relief of one or more symptoms associated with the specific tumor; a reduction in the volume of the tumor; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given tumor can be used to determine whether an effective amount of mirdametinib meets any of these particular endpoints (e.g., CR, PFS, PR).

In certain aspects, a subject is successfully "treated" for cancer, e.g., ovarian cancer, according to the methods described herein if the patient shows one or more of the following: a reduction in the number of or complete absence of cancer cells; relief of one or more symptoms associated with the specific cancer; reduced morbidity and mortality; improvement in quality of life; increased progression-free survival (PFS), disease-free survival (DFS), overall survival (OS), metastasis-free survival (MFS), complete response (CR), minimal residual disease (MRD), partial response (PR), stable disease (SD), a decrease in progressive disease (PD), an increased time to progression (TTP), or any combination thereof. In some aspects, nationally or internationally accepted standards of treatment outcomes in a given cancer can be used to determine whether an effective amount of mirdametinib meets any of these particular endpoints (e.g., CR, PFS, PR).

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See Remington: *The Science and Practice of Pharmacy*, 21st Edition, Lippincott Williams & Wilkins: Philadelphia, P A, 2005; *Handbook of Pharmaceutical Excipients*, 5th Edition, Rowe et al., Eds., The Pharmaceutical Press and the American Pharmaceutical Association: 2005; and *Handbook of Pharmaceutical Additives*, 3rd Edition, Ash and Ash Eds., Gower Publishing Company: 2007; Pharmaceutical Preformulation and Formulation, Gibson Ed., CRC Press LLC: Boca Raton, F L, 2004 (incorporated herein by reference).

The term "pharmaceutically-acceptable salts" refers to the relatively nontoxic, inorganic and organic acid addition salts of mirdametinib. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts. See, e.g., Berge et al. (1977) "Pharmaceutical Salts", J. Pharm. Sci. 66:1-19.

The pharmaceutically acceptable salts of the subject compounds include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, and nitric acid; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, and isothionic.

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Methods of Treatment

One aspect of the present invention relates to a method of treating a patient (e.g., a human patient) 2 years or older who has neurofibromatosis type 1 (NF1) associated inoperable plexiform neurofibromas (PN) by orally administering an effective amount of mirdametinib to the patient, where an amount of mirdametinib is administered on the first day of treatment to provide an $AUC_{0-tau}$ less than 400 ng·h/mL. In one embodiment, the patient continues to be administered the mirdametinib to provide an $AUC_{0-tau}$ less than 400 ng·h/mL. In one embodiment, the patient has symptomatic, inoperable plexiform neurofibromas.

Another embodiment is a method of treating a patient 2 years or older who has NF1 associated inoperable PN that is progressing or causing significant morbidity by orally administering an effective amount of mirdametinib to the patient, where an amount of mirdametinib is administered on the first day of treatment to provide an $AUC_{0-tau}$ less than 400 ng·h/mL. In one embodiment, the patient continues to be administered the mirdametinib to provide an $AUC_{0-tau}$ less than 400 ng·h/mL.

Yet another embodiment is a method of treating a human patient 2 years or older who has neurofibromatosis type 1 (NF1) associated inoperable plexiform neurofibromas (PN) by orally administering on the first day of treatment 1 mg of mirdametinib twice daily to the patient to achieve an $AUC_{0-tau}$ less than 400 ng·h/mL.

Yet another embodiment is a method of treating a human patient 2 years or older who has neurofibromatosis type 1 (NF1) associated inoperable plexiform neurofibromas (PN) comprising orally administering on the first day of treatment 1 mg of mirdametinib twice daily to the patient to provide a $C_{max}$ no more than 40 ng/mL.

Yet another embodiment is a method of treating a human patient 8 years or older who has neurofibromatosis type 1 (NF1) associated inoperable plexiform neurofibromas (PN) comprising orally administering an effective amount of mirdametinib to the patient, wherein an amount of mirdametinib is administered on the first day of treatment to provide (i) an $AUC_{0-tau}$ less than 400 ng·h/mL, (ii) a $C_{max}$ no more than 40 ng/mL, or (iii) both, wherein, during treatment, the patient suffers from acneiform rash and is topically treated (or administered) with clindamycin. In one embodiment, the patient suffers from pustular rash. In one embodiment, the patient continues to be administered the mirdametinib to provide an $AUC_{0-tau}$ less than 400 ng·h/mL.

Yet another embodiment is a method of treating a tumor or cancer in a patient (e.g., a human patient) by orally administering an effective amount of mirdametinib to the patient, wherein an amount of mirdametinib is administered on the first day of treatment to provide (i) an $AUC_{0-tau}$ less than 400 ng·h/mL, (ii) a $C_{max}$ no more than 40 ng/mL, or (iii) both. In one embodiment, the patient continues to be administered the mirdametinib to provide (i) an $AUC_{0-tau}$ less than 400 ng·h/mL, (ii) a $C_{max}$ no more than 40 ng/mL, or (iii) both. In one embodiment, the tumor or cancer is selected from the group consisting of plexiform neurofibromas (PN), plexiform neurofibromas associated with neurofibromatosis type 1 (NF1-PN), high grade glioma (HGG), low grade ovarian cancer, Langerhans cell histiocytosis (LCH), brain cancer, and a cancer that has metastasized to a patient's brain. In one embodiment, the tumor or cancer is plexiform neurofibromas. In another embodiment, the tumor or cancer is plexiform neurofibromas associated with neurofibromatosis type 1. In yet another embodiment, the tumor or cancer is high grade glioma. In yet another embodiment, the high grade glioma is a primary cancer. In yet another embodiment, the high grade glioma is a metastatic cancer. In yet another embodiment, the tumor or cancer is low grade ovarian cancer. In yet another embodiment, the tumor or cancer is Langerhans cell histiocytosis. In yet another embodiment, the tumor or cancer is brain cancer. In yet another embodiment, the tumor or cancer is a cancer that has metastasized to the patient's brain including lung cancer, breast cancer and melanoma.

Yet another embodiment is a method of treating a human patient 2 years or older who has neurofibromatosis type 1 (NF1) associated inoperable plexiform neurofibromas (PN) by orally administering an effective amount of mirdametinib to the patient, where an amount of mirdametinib is administered on the first day of treatment to provide a $C_{max}$ no more than 40 ng/mL.

Yet another embodiment is a method of treating a human patient 2 years or older who has neurofibromatosis type 1 (NF1) associated inoperable plexiform neurofibromas (PN) that is progressing or causing significant morbidity by orally administering an effective amount of mirdametinib to the patient, where an amount of mirdametinib is administered on the first day of treatment to provide a $C_{max}$ no more than 40 ng/mL. In one embodiment, an amount of mirdametinib is administered on the first day of treatment to provide a $C_{max}$ no more than 32 ng/mL. In another embodiment, an amount of mirdametinib is administered on the first day of treatment to provide a $C_{max}$ no more than 30 ng/mL.

Yet another embodiment is a method of treating a human patient at least 2 years of age who has neurofibromatosis type 1 (NF1) associated inoperable plexiform neurofibromas (PN) comprising
(a) selecting mirdametinib as a treatment for the patient at least partially based on its objective response rate, where the objective response rate is defined as at least a 20% decrease in tumor size using centrally read MRI volumetric analysis, and
(b) upon selection of mirdametinib as a treatment, orally administering an effective amount of mirdametinib to the patient. In one embodiment, in step (a), mirdametinib is selected based on a response rate of at least 70%. In another embodiment, in step (i), mirdametinib is selected based on a response rate of at least 75%. In yet another embodiment, in step (i), mirdametinib is selected based on a response rate of at least 80%. In yet another embodiment, in step (i), mirdametinib is selected based on a response rate of at least 85%. In yet another embodiment, in step (i), mirdametinib is selected based on a response rate of at least 90%. In yet another embodiment, in step (i), mirdametinib is selected based on a response rate of at least 95%.

In one embodiment of any of the methods described herein, an amount of mirdametinib is administered on the first day of treatment to provide an $AUC_{0\text{-}tau}$ less than 375, 350, 325, 300, 275, 250, 225, 200, 175, 150, 125, or 100 ng·h/mL. In one embodiment, the patient continues to be administered the mirdametinib to provide an $AUC_{0\text{-}tau}$ less than 375, 350, 325, 300, 275, 250, 225, 200, 175, 150, 125, or 100 ng·h/mL.

In one embodiment of any of the methods described herein, an amount of mirdametinib is administered on the first day of treatment to provide an $AUC_{0\text{-}tau}$ less than 200 ng·h/mL. In one embodiment, the patient continues to be administered the mirdametinib to provide an $AUC_{0\text{-}tau}$ less than 200 ng·h/mL.

In one embodiment of any of the methods described herein, an amount of mirdametinib is administered on the first day of treatment to provide an $AUC_{0\text{-}tau}$ less than 100 ng·h/mL. In one embodiment, the patient continues to be administered the mirdametinib to provide an $AUC_{0\text{-}tau}$ less than 100 ng·h/mL.

In one embodiment of any of the methods described herein, an amount of mirdametinib is administered on the first day of treatment to provide a $C_{max}$ no more than 38, 36, 34, 32, 30, or 28 ng/mL. In another embodiment of any of the methods described herein, an amount of mirdametinib is administered on the first day of treatment to provide a $C_{max}$ no more than 32 ng/mL. In yet another embodiment, an amount of mirdametinib is administered on the first day of treatment to provide a $C_{max}$ no more than 30 ng/mL.

In one embodiment of any of the methods described herein, the patient has symptomatic, inoperable plexiform neurofibromas (PNs).

In one embodiment of any of the methods described herein, the patient has progressive PN.

In one embodiment of any of the methods described herein, the patient has PNs that cause significant morbidity.

In one embodiment of any of the methods described herein, the patient (e.g., NF1-PN patient) has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function, or painful lesions. In one embodiment, the lesions causing major deformity or are significantly disfiguring are tumors of the head and neck or those on other areas of the body that are unable to be concealed by standard garments. In one embodiment of any of the methods described herein, the patient has paraspinal lesions.

In one embodiment of any of the methods described herein, the patient has the clinical diagnosis of NF1 using the NIH Consensus Conference and one or more of the following:
(a) six or more café-au-lait macules with a diameter >5 mm in prepubertal and >15 mm in post-pubertal individuals;
(b) freckling in axilla or inguinal regions;
(c) optic glioma;
(d) two or more Lisch nodules;
(e) a distinctive bony lesion (dysplasia of the sphenoid bone or dysplasia of thinning of long bone cortex); and
(f) a first degree relative with NF1.

In one embodiment of any of the methods described herein, the patient has a constitutional NF1 mutation documented in a Clinical Laboratory Improvement Amendments/College of American Pathologists certified lab.

In one embodiment of any of the methods described herein, the patient either (a) has a parent diagnosed with NF1 and one or more criteria of (1) through (7) or (b) does not have a parent diagnosed with NF1 but has two or more criteria of (1) through (7):
(1) six or more café-au-lait macules over 5 mm in greatest diameter in prepubertal individuals and over 15 mm in greatest diameter in post-pubertal individuals;
(2) freckling in the axillary or inguinal region;
(3) two or more neurofibromas of any type or one plexiform neurofibroma
(4) optic pathway glioma;
(5) two or more iris Lisch nodules identified by slit lamp examination or two or more choroidal abnormalities (defined as bright, patchy nodules imaged by optical coherence tomography (OCT)/near-infrared reflectance (NIR) imaging;
(6) a distinctive osseous lesion (such as sphenoid dysplasia, anterolateral bowing of the tibia, or pseudarthrosis of a long bone); and
(7) a heterozygous pathogenic NF1 variant with a variant allele fraction of 50% in apparently normal tissue such as white blood cells.

In one embodiment of any of the methods described herein,
(a) for a patient having a body surface area no more than 0.69 m², the patient is initially administered 1 mg mirdametinib twice daily,
(b) for a patient having a body surface area of 0.7 to 1.04 m², the patient is initially administered 2 mg mirdametinib twice daily, (c) for a patient having a body surface area of 1.05 to 1.49 m², the patient is initially administered 3 mg mirdametinib twice daily, and
(d) for a patient having a body surface area of at least 1.5 m², the patient is initially administered 4 mg mirdametinib twice daily.

In one embodiment of any of the methods described herein, the initial dosage regimen is continued to be used, unless for instance, a severe adverse event occurs requiring reduction in the dosage regimen.

In one embodiment of any of the methods described herein, the maximum daily dose is 4 mg mirdametinib twice daily.

In one embodiment of any of the methods described herein, over each four week period, the mirdametinib is administered for the first three weeks and discontinued for the last one week.

In one embodiment of any of the methods described herein, the patient has at least a 20% reduction in plexiform neurofibroma volume as determined by volumetric magnetic resonance imaging analysis following treatment with mirdametinib.

In one embodiment of any of the methods described herein, the treatment results in decreased pain intensity.

In one embodiment of any of the methods described herein, the treatment results in decreased pain interference.

In one embodiment of any of the methods described herein, the dose administered is reduced due to an adverse event, wherein the dose is reduced as follows:
(a) if the dose at the time of the event is 1 mg mirdametinib twice daily, then the reduced daily dose is 1 mg administered in the morning only;
(b) if the dose at the time of the event is 2 mg mirdametinib twice daily, then the reduced daily dose is 2 mg administered in the morning and 1 mg administered in the afternoon or evening;
(c) if the dose at the time of the event is 3 mg mirdametinib twice daily, then the reduced daily dose is 2 mg administered twice daily; and
(d) if the dose at the time of the event is 4 mg mirdametinib twice daily, then the reduced daily dose is 3 mg administered twice daily. In one embodiment, the adverse event resulting in the dose reduction is acneiform.

In one embodiment of any of the methods described herein, during treatment, the patient is topically administered clindamycin to treat the acneiform.

In one embodiment of any of the methods described herein, the human patient is at least 2 years of age. In one embodiment, the human patient has an age of ≥2 and <25. In yet another embodiment of any of the methods described herein, the human patient is 2 to 15 years of age. In yet another embodiment of any of the methods described herein, the human patient has an age of ≥2 and 18 years.

In one embodiment of any of the methods described herein, the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis. In one embodiment, in step (i), mirdametinib is selected based on a response rate of at least 70%. In another embodiment, in step (i), mirdametinib is selected based on a response rate of at least 75%. In yet another embodiment, in step (i), mirdametinib is selected based on a response rate of at least 80%. In yet another embodiment, in step (i), mirdametinib is selected based on a response rate of at least 85%. In yet another embodiment, in step (i), mirdametinib is selected based on a response rate of at least 90%. In yet another embodiment, in step (i), mirdametinib is selected based on a response rate of at least 95%.

In some aspects, a therapeutically effective amount of mirdametinib, or a pharmaceutically acceptable salt thereof, is administered. In some aspects, the mirdametinib, or a pharmaceutically acceptable salt thereof, is administered in an amount of about 1 mg/m² to about 10 mg/m² per day based on mirdametinib free base. In some aspects, the mirdametinib, or a pharmaceutically acceptable salt thereof, is administered in an amount of about 1 mg to about 10 mg per day based on mirdametinib free base.

In some aspects, the mirdametinib, or a pharmaceutically acceptable salt thereof, is administered in a single dosage form comprising about 0.1 mg/m² to about 10 mg/m² based on mirdametinib free base. In some aspects, the mirdametinib, or a pharmaceutically acceptable salt thereof, is administered in a single dosage form comprising about 0.1 mg to about 10 mg based on mirdametinib free base.

In some aspects, the mirdametinib, or a pharmaceutically acceptable salt thereof, is administered once daily. In some aspects, the mirdametinib, or a pharmaceutically acceptable salt thereof, is administered twice daily.

In some aspects, the mirdametinib, or a pharmaceutically acceptable salt thereof, exhibits high blood-brain-barrier penetration.

In one embodiment of any of the methods described herein, the human patient has had no prior exposure to MEK inhibitors.

In one embodiment of any of the methods described herein, the mirdametinib, or a pharmaceutically acceptable salt thereof, is administered orally. In some aspects, the mirdametinib, or a pharmaceutically acceptable salt thereof, is dispersible in a potable liquid or orodispersible in a patient's saliva. In some aspects, the mirdametinib, or a pharmaceutically acceptable salt thereof, is administered orally as a solid dosage form. In some aspects, the solid dosage form is a tablet or capsule. In some aspects, the solid dosage form is a capsule.

In one embodiment of any of the methods described herein, the mirdametinib, or a pharmaceutically acceptable salt thereof, is administered as a monotherapy to treat the tumor or cancer. In some aspects, the mirdametinib, or a pharmaceutically acceptable salt thereof, is administered in combination with another active ingredient and/or surgery to treat the tumor or cancer.

In one embodiment of any of the methods described herein, the mirdametinib is mirdametinib free base.

In some aspects, a therapeutically effective amount of mirdametinib, or a pharmaceutically acceptable salt thereof, is administered.

In some aspects, the mirdametinib, or a pharmaceutically acceptable salt thereof, is administered in an amount of about 1 mg/m² to about 10 mg/m² per day based on mirdametinib free base, about 1.5 mg/m² to about 9.5 mg/m² per day based on mirdametinib free base, about 2 mg/m² to about 9 mg/m² per day based on mirdametinib free base, about 2.5 mg/m² to about 8.5 mg/m² per day based on mirdametinib free base, about 3 mg/m² to about 8 mg/m² per day based on mirdametinib free base, about 3.5 mg/m² to about 7.5 mg/m² per day based on mirdametinib free base, about 4 mg/m² to about 7 mg/m² per day based on mirdametinib free base, about 4.5 mg/m² to about 6.5 mg/m² per day based on mirdametinib free base, or about 5 mg/m² to about 6 mg/m² per day based on mirdametinib free base. In some aspects, the mirdametinib, or a pharmaceutically acceptable salt thereof, is administered in an amount of about 1 mg/m² per day based on mirdametinib free base, about 1.5 mg/m² per day based on mirdametinib free base, about 2 mg/m² per day based on mirdametinib free base, about 2.5 mg/m² per day based on mirdametinib free base, about 3 mg/m² per day based on mirdametinib free base, about 3.5 mg/m² per day based on mirdametinib free base, about 4 mg/m² per day based on mirdametinib free base, about 4.5 mg/m² per day based on mirdametinib free base, about 5 mg/m² per day based on mirdametinib free base, about 5.5 mg/m² per day based on mirdametinib free base, about 6 mg/m² per day based on mirdametinib free base, about 6.5 mg/m² per day based on mirdametinib free base, about 7 mg/m² per day based on mirdametinib free base, about 7.5 mg/m² per day based on mirdametinib free base, about 8 mg/m² per day based on mirdametinib free base, about 8.5 mg/m² per day based on mirdametinib free base, about 9 mg/m² per day based on mirdametinib free base, about 9.5 mg/m² per day based on mirdametinib free base, or about 10 mg/m² per day based on mirdametinib free base.

In some aspects, the mirdametinib, or a pharmaceutically acceptable salt thereof, is administered in an amount of about 1 mg to about 10 mg per day based on mirdametinib free base, about 1.5 mg to about 9.5 mg per day based on mirdametinib free base, about 2 mg to about 9 mg per day based on mirdametinib free base, about 2.5 mg to about 8.5 mg per day based on mirdametinib free base, about 3 mg to about 8 mg per day based on mirdametinib free base, about 3.5 mg to about 7.5 mg per day based on mirdametinib free base, about 4 mg to about 7 mg per day based on mirdametinib free base, about 4.5 mg to about 6.5 mg per day based on mirdametinib free base, or about 5 mg to about 6 mg per day based on mirdametinib free base. In some aspects, the mirdametinib, or a pharmaceutically acceptable salt thereof, is administered in an amount of about 1 mg per day based on mirdametinib free base, about 1.5 mg per day based on mirdametinib free base, about 2 mg per day based on mirdametinib free base, about 2.5 mg per day based on mirdametinib free base, about 3 mg per day based on mirdametinib free base, about 3.5 mg per day based on mirdametinib free base, about 4 mg per day based on mirdametinib free base, about 4.5 mg per day based on mirdametinib free base, about 5 mg per day based on mirdametinib free base, about 5.5 mg per day based on mirdametinib free base, about 6 mg per day based on mirdametinib free base, about 6.5 mg per day based on mirdametinib free base, about 7 mg per day based on mirdametinib free base, about 7.5 mg per day based on mirdametinib free base, about 8 mg per day based on mirdametinib free base, about 8.5 mg per day based on mirdametinib free base, about 9 mg per day based on mirdametinib free base, about 9.5 mg per day based on mirdametinib free base, or about 10 mg per day based on mirdametinib free base.

In some aspects, the mirdametinib, or a pharmaceutically acceptable salt thereof, is administered in a single dosage form comprising about 0.1 mg/m² to about 10 mg/m² based on mirdametinib free base, about 0.5 mg/m² to about 9.5 mg/m² based on mirdametinib free base, about 1 mg/m² to about 9 mg/m² based on mirdametinib free base, about 1.5 mg/m² to about 8.5 mg/m² based on mirdametinib free base, about 2 mg/m² to about 8 mg/m² based on mirdametinib free base, about 2.5 mg/m² to about 7.5 mg/m² based on mirdametinib free base, about 3 mg/m² to about 7 mg/m² based on mirdametinib free base, about 3.5 mg/m² to about 6.5 mg/m² based on mirdametinib free base, about 4 mg/m² to about 6 mg/m² based on mirdametinib free base, or about 4.5 mg/m² to about 5.5 mg/m² based on mirdametinib free base. In some aspects, the mirdametinib, or a pharmaceutically acceptable salt thereof, is administered in a single dosage form comprising about 0.1 mg/m² based on mirdametinib free base, about 0.2 mg/m² based on mirdametinib free base, about 0.3 mg/m² based on mirdametinib free base, about 0.4 mg/m² based on mirdametinib free base, about 0.5 mg/m² based on mirdametinib free base, about 1 mg/m² based on mirdametinib free base, about 1.5 mg/m² based on mirdametinib free base, about 2 mg/m² based on mirdametinib free base, about 2.5 mg/m² based on mirdametinib free base, about 3 mg/m² based on mirdametinib free base, about 3.5 mg/m² based on mirdametinib free base, about 4 mg/m² based on mirdametinib free base, about 4.5 mg/m² based on mirdametinib free base, about 5 mg/m² based on mirdametinib free base, about 5.5 mg/m² based on mirdametinib free base, about 6 mg/m² based on mirdametinib free base, about 6.5 mg/m² based on mirdametinib free base, about 7 mg/m² based on mirdametinib free base, about 7.5 mg/m² based on mirdametinib free base, about 8 mg/m² based on mirdametinib free base, about 8.5 mg/m² based on mirdametinib free base, about 9 mg/m² based on mirdametinib free base, about 9.5 mg/m² based on mirdametinib free base, or about 10 mg/m² based on mirdametinib free base.

In some aspects, the mirdametinib, or a pharmaceutically acceptable salt thereof, is administered in a single dosage form comprising about 0.1 mg to about 10 mg based on mirdametinib free base, about 0.5 mg to about 9.5 mg based on mirdametinib free base, about 1 mg to about 9 mg based on mirdametinib free base, about 1.5 mg to about 8.5 mg based on mirdametinib free base, about 2 mg to about 8 mg based on mirdametinib free base, about 2.5 mg to about 7.5 mg based on mirdametinib free base, about 3 mg to about 7 mg based on mirdametinib free base, about 3.5 mg to about 6.5 mg based on mirdametinib free base, about 4 mg to about 6 mg based on mirdametinib free base, or about 4.5 mg to about 5.5 mg based on mirdametinib free base. In some aspects, the mirdametinib, or a pharmaceutically acceptable salt thereof, is administered in a single dosage form comprising about 0.1 mg based on mirdametinib free base, about 0.2 mg based on mirdametinib free base, about 0.3 mg based on mirdametinib free base, about 0.4 mg based on mirdametinib free base, about 0.5 mg based on mirdametinib free base, about 1 mg based on mirdametinib free base, about 1.5 mg based on mirdametinib free base, about 2 mg based on mirdametinib free base, about 2.5 mg based on mirdametinib free base, about 3 mg based on mirdametinib free base, about 3.5 mg based on mirdametinib free base, about 4 mg based on mirdametinib free base, about 4.5 mg based on mirdametinib free base, about 5 mg based on mirdametinib free base, about 5.5 mg based on mirdametinib free base, about 6 mg based on mirdametinib free base, about 6.5 mg based on mirdametinib free base, about 7 mg based on mirdametinib free base, about 7.5 mg based on mirdametinib free base, about 8 mg based on mirdametinib free base, about 8.5 mg based on mirdametinib free base, about 9 mg based on mirdametinib free base, about 9.5 mg based on mirdametinib free base, or about 10 mg based on mirdametinib free base.

In some aspects, the mirdametinib, or a pharmaceutically acceptable salt thereof, is administered one, two, three, or four times per day. In some aspects, the mirdametinib, or a pharmaceutically acceptable salt thereof, is administered once daily. In some aspects, the mirdametinib, or a pharmaceutically acceptable salt thereof, is administered twice daily.

In some aspects, the mirdametinib, or a pharmaceutically acceptable salt thereof, is administered twice daily in an amount of about 0.5 mg/m$^2$ to about 10 mg/m$^2$ based on mirdametinib free base, about 1 mg/m$^2$ to about 9.5 mg/m$^2$ based on mirdametinib free base, about 1.5 mg/m$^2$ to about 9 mg/m$^2$ based on mirdametinib free base, about 2 mg/m$^2$ to about 8.5 mg/m$^2$ based on mirdametinib free base, about 2.5 mg/m$^2$ to about 8 mg/m$^2$ based on mirdametinib free base, about 3 mg/m$^2$ to about 7.5 mg/m$^2$ based on mirdametinib free base, about 3.5 mg/m$^2$ to about 7 mg/m$^2$ based on mirdametinib free base, about 4 mg/m$^2$ to about 6.5 mg/m$^2$ based on mirdametinib free base, about 4.5 mg/m$^2$ to about 6 mg/m$^2$ based on mirdametinib free base, or about 5 mg/m$^2$ to about 6 mg/m$^2$ based on mirdametinib free base. In some aspects, the mirdametinib, or a pharmaceutically acceptable salt thereof, is administered twice daily in an amount of about 0.5 mg/m$^2$ based on mirdametinib free base, about 1 mg/m$^2$ based on mirdametinib free base, about 1.5 mg/m$^2$ based on mirdametinib free base, about 2 mg/m$^2$ based on mirdametinib free base, about 2.5 mg/m$^2$ based on mirdametinib free base, about 3 mg/m$^2$ based on mirdametinib free base, about 3.5 mg/m$^2$ based on mirdametinib free base, about 4 mg/m$^2$ based on mirdametinib free base, about 4.5 mg/m$^2$ based on mirdametinib free base, about 5 mg/m$^2$ based on mirdametinib free base, about 5.5 mg/m$^2$ based on mirdametinib free base, about 6 mg/m$^2$ based on mirdametinib free base, about 6.5 mg/m$^2$ based on mirdametinib free base, about 7 mg/m$^2$ based on mirdametinib free base, about 7.5 mg/m$^2$ based on mirdametinib free base, about 8 mg/m$^2$ based on mirdametinib free base, about 8.5 mg/m$^2$ based on mirdametinib free base, about 9 mg/m$^2$ based on mirdametinib free base, about 9.5 mg/m$^2$ based on mirdametinib free base, or about 10 mg/m$^2$ based on mirdametinib free base.

In some aspects, the mirdametinib, or a pharmaceutically acceptable salt thereof, is administered twice daily in an amount of about 0.5 mg to about 10 mg based on mirdametinib free base, about 1 mg to about 9.5 mg based on mirdametinib free base, about 1.5 mg to about 9 mg based on mirdametinib free base, about 2 mg to about 8.5 mg based on mirdametinib free base, about 2.5 mg to about 8 mg based on mirdametinib free base, about 3 mg to about 7.5 mg based on mirdametinib free base, about 3.5 mg to about 7 mg based on mirdametinib free base, about 4 mg to about 6.5 mg based on mirdametinib free base, about 4.5 mg to about 6 mg based on mirdametinib free base, or about 5 mg to about 6 mg based on mirdametinib free base. In some aspects, the mirdametinib, or a pharmaceutically acceptable salt thereof, is administered twice daily in an amount of about 0.5 mg based on mirdametinib free base, about 1 mg based on mirdametinib free base, about 1.5 mg based on mirdametinib free base, about 2 mg based on mirdametinib free base, about 2.5 mg based on mirdametinib free base, about 3 mg based on mirdametinib free base, about 3.5 mg based on mirdametinib free base, about 4 mg based on mirdametinib free base, about 4.5 mg based on mirdametinib free base, about 5 mg based on mirdametinib free base, about 5.5 mg based on mirdametinib free base, about 6 mg based on mirdametinib free base, about 6.5 mg based on mirdametinib free base, about 7 mg based on mirdametinib free base, about 7.5 mg based on mirdametinib free base, about 8 mg based on mirdametinib free base, about 8.5 mg based on mirdametinib free base, about 9 mg based on mirdametinib free base, about 9.5 mg based on mirdametinib free base, or about 10 mg based on mirdametinib free base.

In some aspects, the mirdametinib, or a pharmaceutically acceptable salt thereof, is administered in a total daily dose that does not exceed about 10 mg/m$^2$ based on mirdametinib free base, about 9.5 mg/m$^2$ based on mirdametinib free base, about 9 mg/m$^2$ based on mirdametinib free base, about 8.5 mg/m$^2$ based on mirdametinib free base, about 8 mg/m$^2$ based on mirdametinib free base, about 7.5 mg/m$^2$ based on mirdametinib free base, about 7 mg/m$^2$ based on mirdametinib free base, about 6.5 mg/m$^2$ based on mirdametinib free base, about 6 mg/m$^2$ based on mirdametinib free base, about 5.5 mg/m$^2$ based on mirdametinib free base, about 5 mg/m$^2$ based on mirdametinib free base, about 4.5 mg/m$^2$ based on mirdametinib free base, about 4 mg/m$^2$ based on mirdametinib free base, about 3.5 mg/m$^2$ based on mirdametinib free base, about 3 mg/m$^2$ based on mirdametinib free base, about 2.5 mg/m$^2$ based on mirdametinib free base, about 2 mg/m$^2$ based on mirdametinib free base, or about 1.5 mg/m$^2$ based on mirdametinib free base.

In some aspects, the mirdametinib, or a pharmaceutically acceptable salt thereof, is administered in a total daily dose that does not exceed about 10 mg based on mirdametinib free base, about 9.5 mg based on mirdametinib free base, about 9 mg based on mirdametinib free base, about 8.5 mg based on mirdametinib free base, about 8 mg based on mirdametinib free base, about 7.5 mg based on mirdametinib free base, about 7 mg based on mirdametinib free base, about 6.5 mg based on mirdametinib free base, about 6 mg based on mirdametinib free base, about 5.5 mg based on mirdametinib free base, about 5 mg based on mirdametinib free base, about 4.5 mg based on mirdametinib free base, about 4 mg based on mirdametinib free base, about 3.5 mg based on mirdametinib free base, about 3 mg based on mirdametinib free base, about 2.5 mg based on mirdametinib free base, about 2 mg based on mirdametinib free base, or about 1.5 mg based on mirdametinib free base.

In some aspects, the mirdametinib, or a pharmaceutically acceptable salt thereof, is administered as mirdametinib free base.

In some aspects, the mirdametinib free base is administered in an amount of about 1 mg/m$^2$ to about 10 mg/m$^2$ per day, about 1.5 mg/m$^2$ to about 9.5 mg/m$^2$ per day, about 2 mg/m$^2$ to about 9 mg/m$^2$ per day, about 2.5 mg/m$^2$ to about 8.5 mg/m$^2$ per day, about 3 mg/m$^2$ to about 8 mg/m$^2$ per day, about 3.5 mg/m$^2$ to about 7.5 mg/m$^2$ per day, about 4 mg/m$^2$ to about 7 mg/m$^2$ per day, about 4.5 mg/m$^2$ to about 6.5 mg/m$^2$ per day, or about 5 mg/m$^2$ to about 6 mg/m$^2$ per day. In some aspects, the mirdametinib free base is administered in an amount of about 1 mg/m$^2$ per day, about 1.5 mg/m$^2$ per day, about 2 mg/m$^2$ per day, about 2.5 mg/m$^2$ per day, about 3 mg/m$^2$ per day, about 3.5 mg/m$^2$ per day, about 4 mg/m$^2$ per day, about 4.5 mg/m$^2$ per day, about 5 mg/m$^2$ per day, about 5.5 mg/m$^2$ per day, about 6 mg/m$^2$ per day, about 6.5 mg/m$^2$ per day, about 7 mg/m$^2$ per day, about 7.5 mg/m$^2$ per day, about 8 mg/m$^2$ per day, about 8.5 mg/m$^2$ per day, about 9 mg/m$^2$ per day, about 9.5 mg/m$^2$ per day, or about 10 mg/m$^2$ per day.

In some aspects, the mirdametinib free base is administered in an amount of about 1 mg to about 10 mg per day, about 1.5 mg to about 9.5 mg per day, about 2 mg to about 9 mg per day, about 2.5 mg to about 8.5 mg per day, about 3 mg to about 8 mg per day, about 3.5 mg to about 7.5 mg per day, about 4 mg to about 7 mg per day, about 4.5 mg to about 6.5 mg per day, or about 5 mg to about 6 mg per day. In some aspects, the mirdametinib free base is administered in an amount of about 1 mg per day, about 1.5 mg per day, about 2 mg per day, about 2.5 mg per day, about 3 mg per day, about 3.5 mg per day, about 4 mg per day, about 4.5 mg per day, about 5 mg per day, about 5.5 mg per day, about 6 mg per day, about 6.5 mg per day, about 7 mg per day, about 7.5 mg per day, about 8 mg per day, about 8.5 mg per day, about 9 mg per day, about 9.5 mg per day, or about 10 mg per day.

In some aspects, the mirdametinib free base is administered in a single dosage form comprising about 0.1 mg/m$^2$ to about 10 mg/m$^2$, about 0.5 mg/m$^2$ to about 9.5 mg/m$^2$, about 1 mg/m$^2$ to about 9 mg/m$^2$, about 1.5 mg/m$^2$ to about 8.5 mg/m$^2$, about 2 mg/m$^2$ to about 8 mg/m$^2$, about 2.5 mg/m$^2$ to about 7.5 mg/m$^2$, about 3 mg/m$^2$ to about 7 mg/m$^2$, about 3.5 mg/m$^2$ to about 6.5 mg/m$^2$, about 4 mg/m$^2$ to about 6 mg/m$^2$, or about 4.5 mg/m$^2$ to about 5.5 mg/m$^2$. In some aspects, the mirdametinib free base is administered in a single dosage form comprising about 0.1 mg/m$^2$, about 0.2 mg/m$^2$, about 0.3 mg/m$^2$, about 0.4 mg/m$^2$, about 0.5 mg/m$^2$, about 1 mg/m$^2$, about 1.5 mg/m$^2$, about 2 mg/m$^2$, about 2.5 mg/m$^2$, about 3 mg/m$^2$, about 3.5 mg/m$^2$, about 4 mg/m$^2$, about 4.5 mg/m$^2$, about 5 mg/m$^2$, about 5.5 mg/m$^2$, about 6 mg/m$^2$, about 6.5 mg/m$^2$, about 7 mg/m$^2$, about 7.5 mg/m$^2$, about 8 mg/m$^2$, about 8.5 mg/m$^2$, about 9 mg/m$^2$, about 9.5 mg/m$^2$, or about 10 mg/m$^2$.

In some aspects, the mirdametinib free base is administered in a single dosage form comprising about 0.1 mg to about 10 mg, about 0.5 mg to about 9.5 mg, about 1 mg to about 9 mg, about 1.5 mg to about 8.5 mg, about 2 mg to about 8 mg, about 2.5 mg to about 7.5 mg, about 3 mg to about 7 mg, about 3.5 mg to about 6.5 mg, about 4 mg to about 6 mg, or about 4.5 mg to about 5.5 mg. In some aspects, the mirdametinib free base is administered in a single dosage form comprising about 0.1 mg, about 0.2 mg, about 0.3 mg, about 0.4 mg, about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg.

In some aspects, the mirdametinib free base is administered one, two, three, or four times per day. In some aspects, the mirdametinib free base is administered once daily. In some aspects, the mirdametinib free base is administered twice daily.

In some aspects, the mirdametinib free base is administered twice daily in an amount of about 0.5 mg/m$^2$ to about 10 mg/m$^2$, about 1 mg/m$^2$ to about 9.5 mg/m$^2$, about 1.5 mg/m$^2$ to about 9 mg/m$^2$, about 2 mg/m$^2$ to about 8.5 mg/m$^2$, about 2.5 mg/m$^2$ to about 8 mg/m$^2$, about 3 mg/m$^2$ to about 7.5 mg/m$^2$, about 3.5 mg/m$^2$ to about 7 mg/m$^2$, about 4 mg/m$^2$ to about 6.5 mg/m$^2$, about 4.5 mg/m$^2$ to about 6 mg/m$^2$, or about 5 mg/m$^2$ to about 6 mg/m$^2$. In some aspects, the mirdametinib free base is administered twice daily in an amount of about 0.5 mg/m$^2$, about 1 mg/m$^2$, about 1.5 mg/m$^2$, about 2 mg/m$^2$, about 2.5 mg/m$^2$, about 3 mg/m$^2$, about 3.5 mg/m$^2$, about 4 mg/m$^2$, about 4.5 mg/m$^2$, about 5 mg/m$^2$, about 5.5 mg/m$^2$, about 6 mg/m$^2$, about 6.5 mg/m$^2$, about 7 mg/m$^2$, about 7.5 mg/m$^2$, about 8 mg/m$^2$, about 8.5 mg/m$^2$, about 9 mg/m$^2$, about 9.5 mg/m$^2$, or about 10 mg/m$^2$.

In some aspects, the mirdametinib free base is administered twice daily in an amount of about 0.5 mg to about 10 mg, about 1 mg to about 9.5 mg, about 1.5 mg to about 9 mg, about 2 mg to about 8.5 mg, about 2.5 mg to about 8 mg, about 3 mg to about 7.5 mg, about 3.5 mg to about 7 mg, about 4 mg to about 6.5 mg, about 4.5 mg to about 6 mg, or about 5 mg to about 6 mg. In some aspects, the mirdametinib free base is administered twice daily in an amount of about 0.5 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, or about 10 mg.

In some aspects, the mirdametinib free base is administered in a total daily dose that does not exceed about 10 mg/m$^2$, about 9.5 mg/m$^2$, about 9 mg/m$^2$, about 8.5 mg/m$^2$, about 8 mg/m$^2$, about 7.5 mg/m$^2$, about 7 mg/m$^2$, about 6.5 mg/m$^2$, about 6 mg/m$^2$, about 5.5 mg/m$^2$, about 5 mg/m$^2$, about 4.5 mg/m$^2$, about 4 mg/m$^2$, about 3.5 mg/m$^2$, about 3 mg/m$^2$, about 2.5 mg/m$^2$, about 2 mg/m$^2$, or about 1.5 mg/m$^2$.

In some aspects, the mirdametinib free base is administered in a total daily dose that does not exceed about 10 mg, about 9.5 mg, about 9 mg, about 8.5 mg, about 8 mg, about 7.5 mg, about 7 mg, about 6.5 mg, about 6 mg, about 5.5 mg, about 5 mg, about 4.5 mg, about 4 mg, about 3.5 mg, about 3 mg, about 2.5 mg, about 2 mg, or about 1.5 mg.

In some aspects, the mirdametinib, or a pharmaceutically acceptable salt thereof, exhibits high blood-brain-barrier penetration.

In some aspects, the human patient has had no prior exposure to MEK inhibitors. In some aspects, the human patient has not responded to prior treatment to one or more MEK inhibitors.

In some aspects, the mirdametinib, or a pharmaceutically acceptable salt thereof, is administered orally. In some aspects, the mirdametinib, or a pharmaceutically acceptable salt thereof, is administered orally as a solid dosage form. In some aspects, the solid dosage form is a tablet or capsule. In some aspects, the solid dosage form is a capsule. In some aspects, the mirdametinib, or a pharmaceutically acceptable salt thereof, is dispersible in a potable liquid or orodispersible in a patient's saliva. In one embodiment, the mirdametinib, or a pharmaceutically acceptable salt thereof, is administered as a dispersible formulation (such as a 0.5 mg or 1 mg mirdametinib dispersible tablet) as described in U.S. Pat. No. 11,571,402, which is hereby incorporated by reference.

In some aspects, the mirdametinib, or a pharmaceutically acceptable salt thereof, is administered as a monotherapy to treat the tumor or cancer.

In some aspects, the mirdametinib, or a pharmaceutically acceptable salt thereof, is administered in combination with another active ingredient and/or surgery to treat the tumor or cancer.

III. Pharmaceutical Compositions

Yet another embodiment is an oral pharmaceutical composition comprising 1.0 mg mirdametinib, where the composition provides, upon initial oral administration to a human subject who has just initiated treatment with mirdametinib, an AUC$_{0-tau}$ less than 400 ng·h/mL. In one embodiment, the composition provides, upon initial oral administration to a human subject who has just initiated treatment with mirdametinib, an AUC$_{0-tau}$ less than 375, 350, 325, 300, 275, 250, 225, 200, 175, 150, 125, or 100 ng·h/mL.

Yet another embodiment is an oral pharmaceutical composition comprising 1.0 mg mirdametinib, where the composition provides, upon initial oral administration to a human subject who has just initiated treatment with mirdametinib, a C$_{max}$ no more than 40 ng/mL. In one embodiment, the composition provides, upon initial oral administration to a human subject who has just initiated treatment with mirdametinib, a C$_{max}$ no more than 38, 36, 34, 32, 30, or 28 ng/mL.

The oral pharmaceutical composition described herein may include one or more pharmaceutically acceptable excipients. The oral pharmaceutical composition may contain one or more diluents, disintegrants, lubricants, or any combination of any of the foregoing. In one embodiment, the oral dosage form comprises (a) about 0.1 w/w % to about 5 w/w % wt/wt % of mirdametinib, (b) about 50 w/w % to about 98 w/w % of one or more diluents; (c) about 1 w/w % to about 10 w/w % of one or more disintegrants; and (d) up to about 5 w/w % of one or more lubricants.

Suitable diluents include, but are not limited to, microcrystalline cellulose, lactose, mannitol, sorbitol, xylitol, sucrose, starch, pregelatinized starch, calcium sulfate, calcium carbonate, dibasic calcium phosphate, and any combination of any of the foregoing. In one embodiment, the oral dosage form includes the diluent microcrystalline cellulose.

Suitable disintegrants include, but are not limited to, croscarmellose sodium, sodium starch glycolate, crospovidone, microcrystalline cellulose, starch, pregelatinized starch, low substituted hydroxypropyl cellulose, alginic acid, and any combination of any of the foregoing. In one embodiment, the oral dosage form includes the disintegrant croscarmellose sodium.

Suitable lubricants include, but are not limited to, magnesium stearate, stearic acid, calcium stearate, zinc stearate, beeswax, colloidal silicon dioxide, hydrogenated vegetable oil, sodium stearyl fumarate, glycerol dibehenate, talc, and any combination of any of the foregoing. In one embodiment, the oral dosage form includes the lubricant magnesium stearate.

The oral pharmaceutical composition can be a capsule, such as a hard gelatin capsule, or a tablet.

EXAMPLE

Example 1: Phase I/II Evaluation of Single Agent Mirdametinib, a Brain-Penetrant MEK1/2 Inhibitor, for the Treatment of Children, Adolescents, and Young Adults with Brain Cancer A multi-arm phase I/II trial of mirdametinib is to be conducted in patients ≥2 and <25 years with brain cancer. Phase I requires participants have no prior exposure to MEK inhibitors and recurrent/progressive disease with biopsy-proven evidence of MAPK pathway activation. Three escalating dose levels (2 mg/m$^2$/dose BID, 2.5 mg/m$^2$/dose BID and 3 mg/m$^2$/dose BID) are planned using a rolling 6 design.

The median age enrolled in the study is 10 years old (3-21). No dose-limiting toxicities occur for all three dose levels. No MEK related retinopathy or cardiopathy is observed. No disease progressions are occurred. Thus far, mirdametinib is well-tolerated and clinically promising when dosed continuously in patients with brain cancer.

Example 2: Phase 2b Trial of Mirdametinib in Adult and Pediatric Patients with Neurofibromatosis Type 1 (NF1)-Associated Inoperable Plexiform Neurofibromas (PNs) that are Progressing or Causing Significant Morbidity This study is to evaluate the efficacy, safety, and tolerability of mirdametinib in participants ≥2 years of age with an inoperable NF1-associated plexiform neurofibromas (PNs) that is progressing and/or causing significant morbidity.

Approximately 120 participants will be screened (assessed for eligibility as described below) to achieve approximately 100 participants assigned to study treatment. Of these participants, approximately 50 will be ≥18 years of age and approximately 50 will be 2 to 17 years of age.

Participants will be screened for up to 28 days prior to the first dose of study treatment mirdametinib. Study treatment will be administered orally at a twice daily (BID) dose specified in the table below. Dosing will be on a 28-day Cycle (4-week course) with a 3 week on/1 week off schedule. The treatment period will last for up to 24 Cycles followed by a 30-day Safety Follow-Up period.

| Subject's BSA (m$^2$) | ≤0.69 | 0.7 to 1.04 | 1.05 to 1.49 | ≥1.5 |
|---|---|---|---|---|
| BID dose (mg) | 1 | 2 | 3 | 4 |

A partial response is defined as PN decrease ≥20% compared to baseline using centrally read MiII volumetric analysis.

Inclusion Criteria

Patients are eligible to be included in the study only if all of the following criteria apply:

1. Participant must be ≥2 years of age inclusive, at the time of signing the informed consent/assent.
2. Participants must have either the clinical diagnosis of NF1 using the National Institute of Health (NIH) Consensus Conference criteria of at least 1 other diagnostic criterion (Inclusion 2.1-2.6, see below) in addition to the presence of PN, or have a constitutional NF1 mutation documented in a Clinical Laboratory Improvement Amendments/College of American Pathologists certified lab; additional criteria are as follows:
    2.1. Six or more café-au-lait macules with a diameter >5 mm in prepubertal and >15 mm in post-pubertal individuals, respectively
    2.2. Freckling in axilla or inguinal regions;
    2.3. Optic glioma;
    2.4. Two or more Lisch nodules;
    2.5. A distinctive bony lesion (dysplasia of the sphenoid bone or dysplasia of thinning of long bone cortex);
    2.6. A first degree relative with NF1.
3. Participants must have PN that is progressive (Inclusion 3.1) OR causing significant morbidity, such as (but not limited to) head and neck lesions that are compromising the airway or great vessels, brachial or lumbar plexus lesions that are causing nerve compression and loss of function, lesions causing major deformity or are significantly disfiguring (Inclusion 3.2), lesions of the extremity that cause limb hypertrophy or loss of function, and painful lesions. Participants with paraspinal PNs will be eligible for this study. Histologic confirmation of tumor is not necessary in the presence of consistent clinical and radiographic findings but should be considered if malignant degeneration of a PN is clinically suspected;
    3.1. For participants enrolled for tumor progression, progression is defined as:
        3.1.1. A measurable increase in PN size (≥20% increase in volume) documented by comparison of two MiII scans in the time period of 12 months or less prior to first dose of study treatment (mirdametinib).
    3.2. For participants enrolled for a "major deformity" or "significantly disfiguring" tumor, eligible tumors will be limited to tumors of the head and neck or those on other areas of the body that are unable to be concealed by standard garments.

4. Participant has a PN that is deemed inoperable, defined as a PN that cannot be completely surgically removed without risk for substantial morbidity due to: encasement of or close proximity to vital structures, invasiveness, or high vascularity of the PN, or the participant refuses surgery. Participants who previously underwent surgery for a PN will be eligible to enter the study after the surgery, provided the PN was incompletely resected and is evaluable by volumetric analysis.
5. Participants must have a target PN, defined as the clinically most relevant PN, amenable to volumetric MM analysis. For the purpose of this study, the target PN must be seen on at least 3 consecutive MM slices and the field of view must contain the entire tumor of interest. As determined by central radiologic review, a target PN must be analyzable by volumetrics, at least 5 mL in volume, and will be classified as "typical PN", "nodular PN", or "solitary nodular PN" prior to first dose of study treatment.
6. Participants ≥18 years of age must have a PN amenable to a percutaneous biopsy and must be willing to undergo pre-, and on treatment tumor biopsies providing fresh tumor tissue; there should be no contraindication for serial biopsy; Patients 2 to 17 years of age should not undergo biopsy unless there is a clinical indication to obtain fresh tumor tissue.
7. Participants ≥16 years of age must have a Karnofsky performance level of ≥60%, and participants <16 years must have a Lansky performance of ≥60%.
8. Participant has adequate organ and bone marrow function as defined by the following screening laboratory values:
   8.1. Absolute neutrophil count ≥1500 cells/μL;
   8.2. Platelets ≥100×10³/μL;
   8.3. Hemoglobin ≥9.5 g/dL;
   8.4. Serum albumin ≥2.8 g/dL;
   8.5. Calculated creatinine clearance at Screening ≥60 mL/min (by Cockcroft-Gault formula) OR a normal serum creatinine based on age described in the table below.

| Age (years) | Maximum Serum Creatinine (mg/dL) |
| --- | --- |
| ≤5 | 0.8 |
| >5 and ≤10 | 1.0 |
| >10 and ≤15 | 1.2 |
| >15 | 1.5 |

9. Participant has the ability to swallow capsules whole.
10. Participant is willing and able to comply with all aspects of the protocol.
11. Participant must weigh at least 10 kg, inclusive, at the time of signing the informed consent/assent.
12. Participant must have a body surface area (BSA) of at least 0.4 m² (inclusive) calculated using the Du Bois formula (BSA=$0.007184 \times w^{0.425} \times H^{0.725}$).
13. Male or Female Contraceptive use by men or women should be consistent with local regulations regarding the methods of contraception for those participating in clinical studies.
   a. Male participants:
   Male participants are eligible to participate if they agree to the following during the treatment period and for at least 90 days after the last dose of study treatment:
      Refrain from donating sperm
      PLUS either:
      Be abstinent from heterosexual intercourse as their preferred and usual lifestyle (abstinent on a long term and persistent basis) and agree to remain abstinent OR
      Must agree to use a male condom when having sexual intercourse with a woman of child bearing potential (WOCBP).
   b. Female participants:
   Female participants are eligible to participate if they are not pregnant or breastfeeding, and at least one of the following conditions applies:
      Is not a woman of childbearing potential
      OR
      Is a WOCBP and using a contraceptive method that is highly effective (with a failure rate of <1% per year), preferably with low user dependency, during the treatment period and for at least 30 days after the last dose of study treatment and agrees not to donate eggs (ova, oocytes) for the purpose of reproduction during the study and for a period of 90 days.
         A WOCBP must have a negative serum pregnancy test result at Screening and a negative urine pregnancy test result at the Baseline visit prior to the first dose of study treatment.

Exclusion Criteria

Participants are excluded from the study if any of the following criteria apply:
1. Participant has a Screening alanine transaminase (ALT) value of >2.0×upper limit of normal (ULN);
2. Participant has a Screening total bilirubin value of >1.5×ULN (isolated bilirubin >1.5×ULN is acceptable if bilirubin is fractionated and direct bilirubin <35%);
3. Participant has a history of malignancy associated hypercalcemia;
4. Participant has an active parathyroid disorder, hyperphosphatemia at Screening (serum phosphorus >1×ULN), and/or serum calcium (mg/dL)×serum phosphorus (mg/dL) product >70 at Screening.
5. Any clinically significant active or known history of liver disease, or known hepatic or biliary abnormalities (with the exception of Gilbert's syndrome or asymptomatic gallstones);
   5.1 Hepatitis serology and viral load will be tested at Screening. Patients who are hepatitis B surface antigen (HBsAg) positive or hepatitis C virus (HCV) antibody positive at Screening must not be enrolled until further definite testing with hepatitis B virus (HBV) deoxyribonucleic acid (DNA) titers is <500 IU/mL or HCV ribonucleic acid (RNA) polymerase chain reaction test is negative;
6. Lymphoma, leukemia, or any malignancy (including malignant glioma or malignant peripheral nerve sheath tumor (MPNST)) within the past 5 years except for basal cell or squamous epithelial carcinomas of the skin that have been resected with no evidence of metastatic disease for 3 years;
7. Breast cancer within the past 10 years;
8. Participants with evidence of an active optic glioma or other low-grade glioma, requiring treatment with chemotherapy or radiation therapy. Participants not requiring treatment are eligible. Ophthalmological findings secondary to long-standing optic pathway glioma (such as visual loss, optic nerve pallor or strabismus) or long-standing orbito-temporal PN (such as visual loss, strabismus) will not be considered a significant abnormality for the purposes of the study;
9. Participant has abnormal QT interval corrected by Fridericia's formula (>450 msec for male participants, >470 msec for female participants, or >480 msec for participants with bundle branch block) after electrolytes have been corrected (triplicate ECG readings taken 2 to 3 minutes apart and averaged) at Screening;
10. Participant has experienced any of the following within 6 months (24 weeks) of signing informed consent/assent: clinically significant cardiac disease, myocardial infarction, severe/unstable angina, coronary/peripheral artery bypass graft, cerebrovascular accident, transient ischemic attack, or symptomatic pulmonary embolism;
11. Participant has ever had a recorded left ventricular ejection fraction (LVEF)<55% as assessed by echocardiogram, OR has a history of congestive heart failure;
12. Participant has a history of, or evidence of, retinal pathology on ophthalmologic examination that is considered a risk factor for central serous retinopathy, retinal vein occlusion (RVO), or neovascular macular degeneration. Participants will be excluded from study participation if they currently are known to have any of the following risk factors for RVO:
    12.1 Intraocular pressure ≥21 mmHg;
    12.2 Serum cholesterol >300 mg/dL;
    12.3 Serum triglycerides >300 mg/dL;
    12.4 Hyperglycemia (fasting blood glucose >125 mg/dL or random blood glucose >200 mg/dL);
    12.5 Age specific hypertension
        i. Participants ≥13 years of age with a blood pressure ≥140/90 mm Hg
        ii. Participants ≤12 years of age with a blood pressure ≥95th percentile for age+12 mmHg;
13. Participant has a history of glaucoma;
14. Participant has a history of a positive human immunodeficiency virus (HIV) antibody test;
15. Participant has a known malabsorption syndrome or preexisting gastrointestinal conditions that may impair absorption of mirdametinib (e.g., gastric bypass, lap band, or other gastric procedures). Delivery of mirdametinib via nasogastric tube or gastrostomy tube is not allowed.
16. Participant has received NF1 PN-targeted therapy (e.g., MEK inhibitors, farnesyltransferase inhibitors, kinase inhibitors, etc.) within 28 days of first dose of study treatment (or 5.5 half-lives, whichever is longer). If participant enrolls with progression and no associated morbidities, NF1-targeted therapy must not be administered after the observed progression (Inclusion Criterion 3.1.1). All toxicities from prior therapy must resolve to ≤Grade 1 or Baseline;
17. Participant previously received or is currently receiving therapy with mirdametinib;
18. Participant is receiving systemic or ocular glucocorticoid therapy (with the exception of participants with endocrine deficiencies who are allowed to receive physiologic or stress doses of steroids, if necessary) within 14 days prior to first dose of study treatment;
19. Participant has received radiation therapy within the 6 months prior to signing of informed consent/assent. Participants who have received radiation to the orbit at any time are excluded;
20. Current enrollment or past participation in any other clinical study (excluding observational studies) within 28 days of signing of informed consent/assent;
21. Participant is unable to tolerate MRI or for whom MRI is contraindicated;
22. Tumor is not able to be reliably evaluated by MRI volumetric analysis;
23. Sensitivity to the study treatment, or components thereof, or drug or other allergy that, in the opinion of the investigator or medical monitor, contraindicates participation in the study;
24. Participant with active bacterial, fungal, or viral infection including but not limited to the use of antibiotics, antifungals, or antiviral agents at the time of screening;
25. Underlying medical conditions, laboratory abnormality, or alcohol or drug abuse or dependence that, in the investigator's opinion, will be unfavorable for the administration of study treatment or affect the explanation of drug toxicity or adverse events; or insufficient compliance during the study according to investigator's judgement; or
26. Participant has experienced other severe acute or chronic medical or psychiatric conditions, including recent (within 1 year of signing informed consent/assent) or active suicidal ideation or behavior, or a laboratory abnormality that may increase the risk associated with study participation or study treatment administration or may interfere with the interpretation of study results and, in the judgment of the Investigator, would make the participant inappropriate for entry into this study.

Supportive Care

Dermatologic Adverse Events:

The use of medications for the supportive care of rash is permitted. Early initiation of treatment for rashes is strongly recommended to minimize the duration and severity of the adverse event.

Acneiform rash: Pustular rash may be treated with topical clindamycin gel or lotion applied BID. In severe cases, semisynthetic oral tetracyclines such as doxycycline or minocycline may also be useful for older children, adolescents, and adults, but should be avoided in children younger than 8 years old because of risk to tooth development.

Eczematous rash/xerosis: Eczematous/dry skin rash and other macular (non-acneiform) rash should be treated with a moisturizer such as Cerave or Eucerin or another equivalent product. A low potency topical steroid such as betamethasone valerate lotion (0.05%), desonide cream (0.05%), fluocinolone acetonide solution (0.01%), dexamethasone sodium phosphate cream (0.1%), hydrocortisone acetate cream (1%), methylprednisolone acetate cream (0.25%) or equivalent may also be used if symptomatic.

Ketoconazole shampoo should be used for any rash involving the scalp.

Paronychia: Paronychia if acute and non-surgical (i.e., no fluctuance suggesting an abscess) can resolve with warm soaks only applied 3 to 4 times daily. If there is extensive redness suggesting cellulitis, OR if there is non-surgical paronychia but the participant is a diabetic or is immunocompromised, then an oral antibiotic that covers *Staphylococcus aureus* should be started. The choice of antibiotics includes a *Staphylococcus aureus* covering penicillin/clindamycin/first generation cephalosporin/Augmentin (amoxicillin and clavulanate).

If an abscess develops, surgical treatment with incision and drainage with or without debridement should be done.

Any infectious organisms identified should be treated accordingly. If the participant has diabetes or is immune compromised, oral antibiotics ensuring coverage for Staphylococcal *aureus* (see above) should be started prior to a culture and sensitivity report. Once culture report is obtained, the antibiotic therapy should be adjusted as appropriate.

Prohibited or Restricted Concomitant Medications/Treatments

Prior use of mirdametinib is prohibited.

Alternative therapy for the treatment of PNs (e.g. MEK inhibitors, farnesyltransferase inhibitors, kinase inhibitors, etc.) within 28 days (or 5.5 half-lives, whichever is longer) of first dose of study treatment and throughout the treatment period is prohibited. If participant enrolls with progression and no associated morbidities, NF1-targeted therapy must not be administered after the observed progression (Inclusion Criterion 3.1.1)

Medical treatment (e.g. chemotherapy, biologic therapy, radiation therapy) directed towards any NF1-related tumor such as optic pathway glioma is prohibited throughout the treatment period.

The use of chronic systemic or ocular glucocorticoid therapy is prohibited within the 14 days prior to first dose of study treatment and throughout the treatment period (with the exception of participants with endocrine deficiencies who are allowed to receive physiologic or stress doses of steroids, if necessary). In addition, corticosteroids are permissible as premedication for blood product transfusions, or as treatment for an acute allergic reaction or bronchospasm.

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

What is claimed:

1. A method of treating a human patient 2 years or older who has neurofibromatosis type 1 (NF1) associated inoperable plexiform neurofibromas (PN) comprising orally administering an effective amount of mirdametinib to the patient, wherein an amount of mirdametinib is administered on the first day of treatment to provide an $AUC_{0\text{-}tau}$ less than 300 ng·h/mL.

2. The method of claim 1, wherein the patient has symptomatic, inoperable plexiform neurofibromas.

3. A method of treating a human patient 2 years or older who has neurofibromatosis type 1 (NF1) associated inoperable plexiform neurofibromas (PN) that is progressing or causing significant morbidity comprising orally administering an effective amount of mirdametinib to the patient, wherein an amount of mirdametinib is administered on the first day of treatment to provide an $AUC_{0\text{-}tau}$ less than 300 ng·h/mL.

4. The method of claim 1, wherein an amount of mirdametinib is administered on the first day of treatment to provide an $AUC_{0\text{-}tau}$ less than 200 ng·h/mL.

5. The method of claim 1, wherein an amount of mirdametinib is administered on the first day of treatment to provide an $AUC_{0\text{-}tau}$ less than 100 ng·h/mL.

6. The method of claim 1, wherein the patient has progressive PN.

7. The method of claim 1, wherein the patient has PNs that cause significant morbidity.

8. The method of claim 1, wherein the patient has head and neck lesions that are compromising the airway or great vessels, brachial or lumbar plexus lesions that are causing nerve compression and loss of function, lesions causing major deformity or are significantly disfiguring, lesions of the extremity that cause limb hypertrophy or loss of function, or painful lesions.

9. The method of claim 8, wherein the lesions causing major deformity or are significantly disfiguring are tumors of the head and neck or those on other areas of the body that are unable to be concealed by standard garments.

10. The method of claim 1, wherein the patient has paraspinal lesions.

11. The method of claim 1, wherein the patient has the clinical diagnosis of NF1 using the NIH Consensus Conference and one or more of the following:
    (a) six or more café-au-lait macules with a diameter >5 mm in prepubertal and >15 mm in post-pubertal individuals;
    (b) freckling in axilla or inguinal regions;
    (c) optic glioma;
    (d) two or more Lisch nodules;
    (e) a distinctive bony lesion (dysplasia of the sphenoid bone or dysplasia of thinning of long bone cortex); and
    (f) a first degree relative with NF1.

12. The method of claim 1, wherein the patient has a constitutional NF1 mutation documented in a Clinical Laboratory Improvement Amendments/College of American Pathologists certified lab.

13. The method of claim 1, wherein the patient either (a) has a parent diagnosed with NF1 and one or more criteria of (1) through (7) or (b) does not have a parent diagnosed with NF1 but has two or more criteria of (1) through (7):
    (1) six or more café-au-lait macules over 5 mm in greatest diameter in prepubertal individuals and over 15 mm in greatest diameter in post-pubertal individuals;
    (2) freckling in the axillary or inguinal region;
    (3) two or more neurofibromas of any type or one plexiform neurofibroma
    (4) optic pathway glioma;
    (5) two or more iris Lisch nodules identified by slit lamp examination or two or more choroidal abnormalities (defined as bright, patchy nodules imaged by optical coherence tomography (OCT)/near-infrared reflectance (NIR) imaging;
    (6) a distinctive osseus lesion (such as sphenoid dysplasia, anterolateral bowing of the tibia, or pseudarthrosis of a long bone); and
    (7) a heterozygous pathogenic NF1 variant with a variant allele fraction of 50% in apparently normal tissue such as white blood cells.

14. The method of claim 1, wherein
(a) for a patient having a body surface area no more than 0.69 m², the patient is initially administered 1 mg mirdametinib twice daily,
(b) for a patient having a body surface area of 0.7 to 1.04 m², the patient is initially administered 2 mg mirdametinib twice daily,
(c) for a patient having a body surface area of 1.05 to 1.49 m², the patient is initially administered 3 mg mirdametinib twice daily, and
(d) for a patient having a body surface area of at least 1.5 m², the patient is initially administered 4 mg mirdametinib twice daily.

15. The method of claim 1, wherein the maximum daily dose is 4 mg mirdametinib twice daily.

16. The method of claim 13, wherein over each four week period, the mirdametinib is administered for the first three weeks and discontinued for the last one week.

17. The method of claim 1, wherein the patient has at least a 20% reduction in plexiform neurofibroma volume as determined by volumetric magnetic resonance imaging analysis following treatment with mirdametinib.

18. The method of claim 1, wherein the treatment results in decreased pain intensity.

19. The method of claim 1, wherein the treatment results in decreased pain interference.

20. The method of claim 13, wherein the dose administered is reduced due to an adverse event, wherein the dose is reduced as follows:
(a) if the dose at the time of the event is 1 mg mirdametinib twice daily, then the reduced daily dose is 1 mg administered in the morning only;
(b) if the dose at the time of the event is 2 mg mirdametinib twice daily, then the reduced daily dose is 2 mg administered in the morning and 1 mg administered in the afternoon or evening;
(c) if the dose at the time of the event is 3 mg mirdametinib twice daily, then the reduced daily dose is 2 mg administered twice daily; and
(d) if the dose at the time of the event is 4 mg mirdametinib twice daily, then the reduced daily dose is 3 mg administered twice daily.

21. The method of claim 20, wherein the adverse event resulting in the dose reduction is acneiform.

22. The method of claim 21, wherein, during treatment, the patient is topically administered clindamycin to treat the acneiform.

23. The method of claim 1, wherein the patient is 2 to 15 years of age.

24. A method of treating a human patient 2 years or older who has neurofibromatosis type 1 (NF1) associated inoperable plexiform neurofibromas (PN) comprising orally administering on the first day of treatment 1 mg of mirdametinib twice daily to the patient to achieve an $AUC_{0\text{-}tau}$ less than 300 ng·h/mL.

25. The method of claim 1, wherein the method further comprises prior to treatment (i) determining whether to select mirdametinib as a treatment for the patient, and (ii) selecting mirdametinib as a treatment for the patient at least partially based on its objective response rate, where the objective response rate is defined as at least a 20% decrease in tumor size using centrally read MRI volumetric analysis.

26. The method of claim 25, wherein in step (i), mirdametinib is selected based on a response rate of at least 70%.

* * * * *

UNITED STATES PATENT AND TRADEMARK OFFICE
CERTIFICATE OF CORRECTION

| | | Page 1 of 1 |
|---|---|---|
| PATENT NO. | : 11,806,322 B2 | |
| APPLICATION NO. | : 18/185148 | |
| DATED | : November 7, 2023 | |
| INVENTOR(S) | : Iloeje et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this
First Day of July, 2025

Coke Morgan Stewart
*Acting Director of the United States Patent and Trademark Office*